US006564076B1

(12) United States Patent
Chance

(10) Patent No.: US 6,564,076 B1
(45) Date of Patent: **\*May 13, 2003**

(54) TIME-RESOLVED SPECTROSCOPIC APPARATUS AND METHOD USING STREAK CAMERA

(75) Inventor: Britton Chance, Marathon, FL (US)

(73) Assignee: Non-Invasive Technology, Inc., Philadelphia, PA (US)

(\*) Notice: Subject to any disclaimer, the term of this patent is extended or adjusted under 35 U.S.C. 154(b) by 0 days.

This patent is subject to a terminal disclaimer.

(21) Appl. No.: 09/717,790

(22) Filed: Nov. 21, 2000

Related U.S. Application Data

(63) Continuation of application No. 07/876,364, filed on Apr. 30, 1992, now Pat. No. 6,192,260, which is a continuation of application No. 07/287,847, filed on Dec. 21, 1988, now Pat. No. 5,119,815.

(51) Int. Cl.[7] .............................. A61B 6/00; A61B 19/00
(52) U.S. Cl. ................. 600/310; 600/322; 600/323; 600/326; 600/340; 600/473; 356/39; 356/40; 356/341; 356/484
(58) Field of Search ................................ 600/310, 407, 600/425, 430, 473, 476, 322, 323, 324–340; 356/319–41, 341–343, 484

(56) References Cited

U.S. PATENT DOCUMENTS

| 4,167,331 A | | 9/1979 | Nielsen |
| 4,556,057 A | | 12/1985 | Hiruma et al. |
| 4,675,529 A | | 6/1987 | Kushida |
| 4,832,034 A | | 5/1989 | Cho et al. |
| 4,832,035 A | | 5/1989 | Cho et al. |
| 5,088,493 A | | 2/1992 | Giannini |
| 5,119,815 A | \* | 6/1992 | Chance .................. 600/342 |
| 5,137,355 A | \* | 8/1992 | Barbour et al. .............. 600/475 |
| 5,792,051 A | \* | 8/1998 | Chance .................. 600/476 |
| 6,192,260 B1 | \* | 2/2001 | Chance .................. 356/41 |

OTHER PUBLICATIONS

Chance, "Comparison of time–resolved and –unresolved measurements of deoxyhemoglobin in brain"; *Proc. Nat. Acad. Sci. USA;* vol. 85, pp 4971–4975 (1988).
Bonner et al., "Model for Photon Migration in Tirbiel Biological Media"; *Japt Soc. Am;* vol. 4, No. 3 (1987).
Delpy et al., "Estimation of optical pathlength through tissue from direct time of flight measurement"; *Phys. Med. Biol.,* 33:1433–1442 (1988).
Chance, *Rev. Sci. Instrum.;* 22:619–627 (1951).
Chance, *Biochemistry of Copper;* ed. Piesach, J. (Academic, New York), pp 293–303 (1966).
Chance, Legallais, V. & Schoener, B., *Nature;* 195:1073–1075 (1962).
Chance, *Science;* 120:767–775 (1954).
Chance, *J. Biol. Chem.;* 234:3036–3040 (1959).

(List continued on next page.)

*Primary Examiner*—David M. Shay
(74) *Attorney, Agent, or Firm*—Fish & Richardson P.C.

(57) ABSTRACT

Methods and apparatus using the principles of time-resolved spectroscopy are disclosed. The present invention employs incident light pulses of sufficiently short duration to permit the rate of the rise and decay of such pulses to be measured. Consequently, the rate of decay, u, permits a determination of the concentration of an absorptive pigment, such as hemoglobin. The present invention also allows the precise path length the photons travel to be determined. Using this path length information and by measuring changes in optical density using known continuous light (CW) spectrophotometry systems, the methods and apparatus disclosed allow changes in the concentration of an absorptive pigment to be correctly be measured. From these data, the oxygenation state of a tissue region, such as the brain, can be accurately determined in real time.

22 Claims, 10 Drawing Sheets

Skull and Brian Log Fit with/without Hb
90°, 760 nm

OTHER PUBLICATIONS

Jobsis–VanderVliet, F.F., *Adv. Exp. Med. Biol.;* 191:833–842 (1985).

Jobsis, F.F., Keizer, J.H., LaManna, J.C. & Rosenthal, M., *J. Appl. Physiol;* 113:858–872 (1977).

Rosenthal, M., LaManna, J.C., Jobsis, F.F., Levasseur, J.E., Kontos, H.A. & Patterson, J.L., *Brain Res.;* 108:143–154 (1976).

VanderZee, P. & Delpy, D.T., in *Oxygen Transport to Tissue X*, eds. Mochizuki, M., Honig, C.R., Koyama, T., Goldstick, T.K. & Bruley, D.F. (Plenum, New York, pp 191–197 (1988).

Tamura, M.H., Hazeki, O., Nioka, S., Chance, B. & Smith, D.S., in *Chemoreceptors and Reflexes in Breathing*, ed. Lahiri, S. (Oxford, New York), in press (1987).

Duysens, L., *Prog. Biophys. Mol. Biol.:* 14:1–104 (1964).

Chance, *Nature* (London); 169:215–230 (1952).

Blumberg, W.E., *Biophys. J.;* 51:288 (abst.) (1987).

Bonner, R.F., Nossal, R., Havlin, S. & Weiss, G.H., *J. Opt. Soc. Am. Sec. A;* 4:423–432 (1987).

Galeotti et al., (Eds.), Membrane in Cancer Cells, 551 *N.Y. Acad. Sci.* (preface) (1988).

Haar et al., "Determination of the Rotational Diffusion by a Picosecond Phase Fluorometer"; *Chem. Phys.;* 49:563–567 (1977).

* cited by examiner

Cat Head Hb 760/790 90°

Skull and Brain with Hemoglobin
90°, 760 and 790 nm

| Sample(Fig) | λ nm | Angle. | Distance. mm | Half-width.ps | μ. cm⁻¹ | L1'2 cm |
|---|---|---|---|---|---|---|
| Water | 760 | - | - | 40 | - | - |
| Milk substitute | 760 | 110 | 65 | 110 | 0.088 | 3.4 |
| −HbO₂ | 760 | 110 | 65 | 150 | 0.083 | 3.6 |
| +Hb | 760 | 110 | 65 | 108 | 0.105 | 2.8 |
| +Hb | 790 | 110 | 65 | 105 | 0.088 | 3.4 |
| −HbO₂ | 790 | 110 | 65 | 142 | 0.081 | 3.7 |
| Cat head(5) | 760 | 90 | 42 | 450 | 0.068 | 4.5 |
| −Hb(5) | 760 | 90 | 42 | 350 | 0.081 | 3.4 |
| −Hb(5) | 790 | 90 | 42 | 430 | 0.072 | 4.2 |
| −Hb(5) | 760 | 90 | 42 | 350 | 0.084 | 3.6 |
| −Hb(5) | 790 | 90 | 42 | 470 | 0.054 | 5.6 |
| Cat brain | 760 | 60 | 24 | 300 | 0.114 | 3.6 |
| | 790 | 60 | 24 | 300 | 0.117 | 3.6 |
| | 790 | 90 | 42 | 290 | 0.090 | 3.3 |

*FIG. 14*

TIME-RESOLVED SPECTROSCOPIC APPARATUS AND METHOD USING STREAK CAMERA

CROSS-REFERENCE TO RELATED APPLICATIONS

This is a continuation of U.S. application Ser. No. 07/876,364 filed on Apr. 30, 1992, now U.S. Pat. No. 6,192,260, which is a continuation of U.S. application Ser. No. 07/287,847, filed Dec. 21, 1988, now U.S. Pat. No. 5,119,815.

This application is related to co-pending applications, Ser. No. 266,166, filed Nov. 2, 1988, in the name of Britton Chance, entitled, "Optical Coupling System for Use in Monitoring Oxygenation State Within Living Tissue", which is hereby incorporated by reference as if fully set forth herein; and Ser. No. 266,019, filed Nov. 2, 1988, in the name of Britton Chance, entitled, "A User-Wearable Hemoglobinometer For Measuring the Metabolic Condition of a Subject", which is hereby incorporated by reference as if fully set forth herein.

BACKGROUND OF THE INVENTION

The present invention relates to methods an apparatus for determining the concentration of tissue pigments, such as hemoglobin, using time-resolved pulses of light. The present invention relies upon the decay characteristics associated with absorptive pigments to derive their concentrations.

The utility of optical methods for studying metabolism and oxidative processes in cells and tissues was significantly enhanced in the early 1950's when time-sharing dual-wavelength systems were developed for the quantitation of small changes in the absorption of light in the visible and near-infrared (NIR) regions in highly scattering media, such as cell suspensions or muscle tissues. See Chance, B. *Rev. Sci. Instrum.* 22,619–627 (1951); Chance B. *Biochemistry of Copper*, ed. Peisach, J. (Academic, New York), pp. 293–303 (1966), which are incorporated by reference as if fully reproduced herein. Fluorescence signals from mitochondrial NADH complemented the absorption method for studies of the surface of heart, brain, and skeletal tissue. See Chance, B., et al., *Nature* (London) 195, 1073–1075 (1962) and Chance B. *Science* 120, 767–775 (1954). NIR spectroscopy has been used to detect the redox state of the copper component of cytochrome oxidase in mitochondria and yeast cells. See Chance, B. *Biochemistry of Cooper*, ed. Peisach, J. (Academic, New York), pp. 293–303 (1966); Chance, B. *J. Biol. Chem* 234, 3036–3040 (1959). Jobsis-Vander Vliet and coworkers pioneered the study of NIR absorption in tissue by transillumination. See Jobsis-Vander Vliet, F. F. *Adv. Exp. Med. Biol.* 191, 833–842 (1985); Jobsis-Vander Vliet, F. F., et al., *J. Appl. Physiol.* 113, 858,872 (1977); see also Rosenthal, M., et al., *Brain Res.* 108, 143–154 (1976). Algorithms have been developed to compensate for the interference from hemoglobin and myoglobin with cytochrome copper, as the latter may constitute as little as 5% of the total signal at 830 nm. See vanderZee. P. & Delpy, D. T. (1988) *Oxygen Transport to Tissue X*, eds. Mochizuki, M., et al., (Plenum, New York), pp. 191–197); see also Tamura, M. H., et al., *Chemoreceptors and Reflexes in Breathing*, ed. Lahiri, S. (Oxford, New York), in press.

An application of the principles of spectrophotometry is the use of continuous light (CW) illumination to determine the attenuation characteristic of light in systems containing localized deoxyhemoglobin (Hb) and to observe hypoxia in the brain. However, although CW systems can be used to quantify changes in optical density, they cannot quantify the concentration of an absorptive pigment.

The change in intensity of light, or the optical density (log $I_o/I$), in an absorbing medium generally follows the Beer-Lambert Law:

$$\log \frac{I_o}{I} = ECL$$

where I is the intensity of light, E is the extinction coefficient, C is the concentration of an absorptive pigment in the medium, L is the optical path length, and the absorption per unit length is defined as $u=EC=1/L$ (log $I_o/I$). This law is the basis for modern spectrophotometry and, as well known to those of ordinary skill, has been repeatedly verified by both research and in industrial applications. The Beer-Lambert Law requires the determination of at least one of two quantities—specific absorption or path length—in addition to intensity. Since CW systems can only quantify changes in intensity, only the product uL can be determined.

When light is directed into an absorptive medium such as a tissue region, it is scattered, reflected, or it migrates from one point to another by a random walk or other diffusion process. The actual length traversed may be the distance between the light input and output in a rectilinear direction, since little or no light is believed to move in an orthogonal direction, except where florescence or other processes may be involved. Under these conditions, CW systems thus cannot independently quantify the specific absorption for a given medium. Therefore, the determination of the concentration of an absorptive pigment must necessarily be carried out by arbitrary calibrations using media of known values of CE in order to determine the relationship between optical density (OD) and path length (L). After L has been determined, the system can then be used to determine subsequent variations in the concentration of the absorptive pigment within a tissue region. This is the general method by which CW absorption spectrometry is carried out with scattering materials. Often, information concerning L is obtained at an adjacent wavelength, such as an isosbestic point. This method is particularly effective when two values of L are similar leading to what is termed precise dual wavelength spectrophotometry of biological tissue. See, for example, the system disclosed in U.S. patent application Ser. No. 266,166, filed Nov. 2, 1988, entitled, "Optical Coupling System For Use In Monitoring Oxygenation State Within Living Tissue", which is incorporated herein by reference as if fully reproduced herein.

Difficulties arise, however, when C for an absorptive material cannot be varied in a rational or known manner. For example, in living tissues, a known change in concentration, C, of an absorptive pigment such as hemoglobin may be difficult to impose, and if imposed, may result in traumatic consequences to the subject. In the case of limbs, tourniquet ischemia can be used to cause a known change in the concentration of hemoglobin, but individual variations and physiological adaptations may falsify any calibrations made. In the brain and heart, where oxygenation data are most needed, it is not possible to calibrate by large perturbations of the system, since damage or death might result. Under these conditions, it is difficult to calibrate the meaning of the trends in observations that may occur in some diseases such as neonatal hypoxia or adult stroke. Thus, the calibration method described loses its force and reliability. Similarly, although animal models have been resorted to for purposes of calibration, since the boundary conditions for photon migration—which are crucial—are likely to differ between the animal model and a human subject, these methods have also generally proven unsatisfactory.

SUMMARY OF THE INVENTION

Accordingly, it has now been found that the concentration of an absorptive pigment in a scattering medium can be quantitatively determined, thereby allowing the path length within the medium to be calibrated. The present invention discloses methods of determining the concentration of a tissue pigment with a known absorption spectrum by illuminating a portion of a tissue region at a first location with a pulse of light having a known duration. The migration of the pulse of light through the tissue region to a second location remote from the first location is then detected, and occurs as a rise to a maximum value and thereafter a decay in the intensity of light at the second location. The rate of decay of the light at the second location is determined; and is expressed as: $-1/(L (\log I))$. This quantity is proportional to the concentration of a tissue pigment with a known absorption spectrum. Finally, the rate of decay, u, is divided by the extinction coefficient (E) to determine the concentration (C) of a particular tissue pigment with a known absorption spectrum.

The present invention is preferably used to determine the concentration of tissue pigments with known extinction coefficients such as hemoglobin, oxyhemoglobin, deoxyhemoglobin, or myoglobin.

In a preferred embodiment, the duration of the input pulse of light is less than about one nanosecond, and most preferably is about 6 picoseconds.

The methods of the present invention are useful for determining the concentration of tissue pigments in living tissue, and further, allow the concentration to be determined substantially instantaneously.

In use, the methods of the present invention preferably place the input pulse and output detector in proximity with the outer surface of the tissue region being studied. Most preferably, the location of the output detector is displaced from the location of the input pulse by a distance of at least several centimeters. Thus, the input pulse enters the tissue region and migrates to the adjacent output detector.

The methods of the present invention preferably include displaying the concentration of a tissue pigment with a known absorption spectrum as an absolute value from which the oxygen content of said region of tissue is determined.

The present invention also discloses apparatus comprised of a laser system capable of generating short pulses of light, transmitting them to the subject, detecting the photons after they have migrated through the subject, determining the rate of decay of the photons and processing the data collected into a final data set representing the concentration of an absorptive pigment having known absorptive characteristics.

BRIEF DESCRIPTION OF THE DRAWINGS

FIG. 14 contains data, presented in Table 1, derived from models and experiments described below.

DETAILED DESCRIPTION

Figure 1:
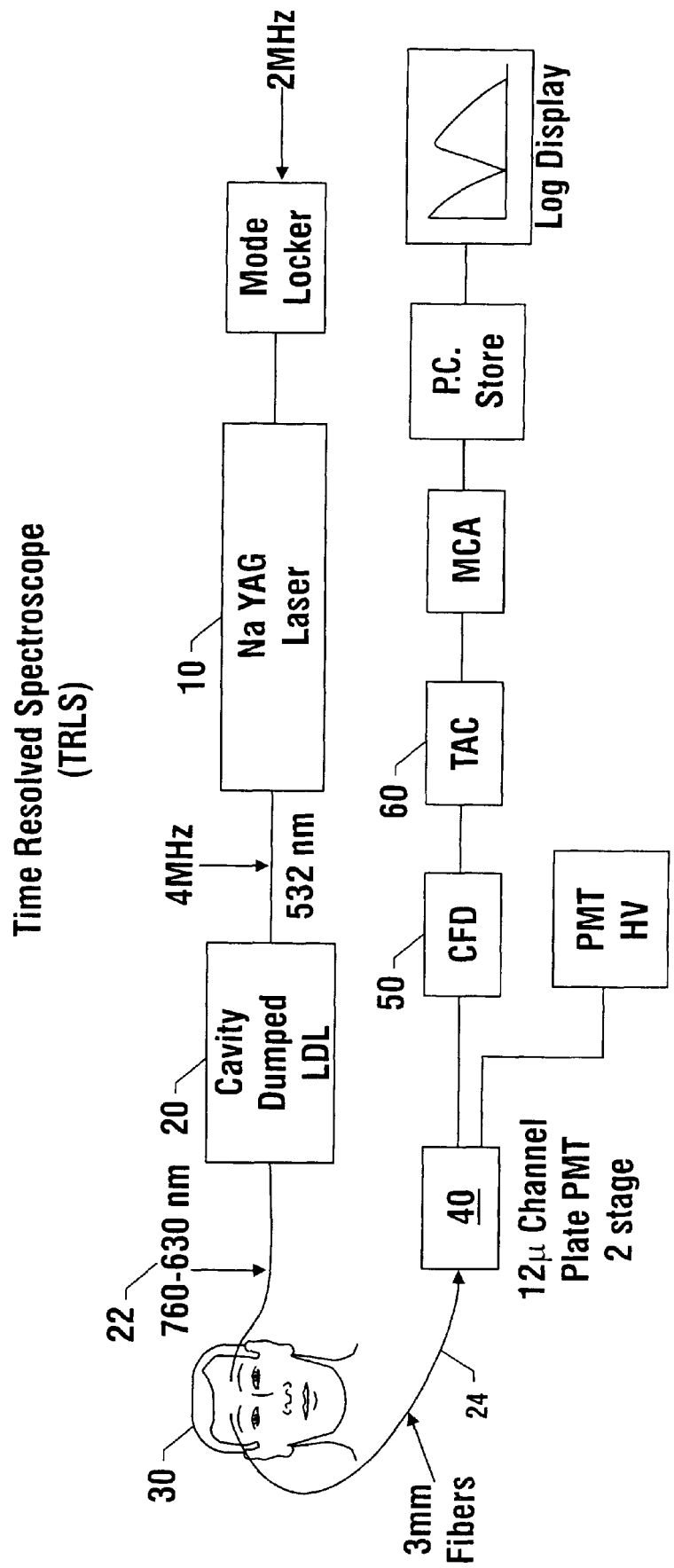
FIG. 1 is a block diagram of preferred apparatus for carrying out the methods of the present invention.

The time resolved or pulsed light spectroscopy of the present invention differs fundamentally from the continuous light (CW) spectroscopy described above. When the pulse duration of light entering a subject is sufficiently short compared to the time of traverse between input and exit, the distance travelled by the photons may be measured quantitatively. Under such conditions L, the distance traversed to the exit, and u, the absorption per unit length, can be determined.

By arranging the expression of the Beer-Lambert Law set forth above with the known quantities on the left, an equation for u results:

$$\frac{1}{L} \log \frac{I_o}{I} = u$$

This equation simply states that the absorption coefficient of a scattering medium which follows the Beer-Lambert Law is directly determined from the logarithm of $I_o/I$ with the change in the path length, L. A simple case occurs at a time long after the decay of the input pulse, where the output photons are only those which have been migrating within the tissue region being studied and are exiting therefrom.

The methods and apparatus of the present invention are based on the concept that path length can be measured when incident light pulses of sufficiently short duration are employed, and the measurements of u mentioned above are made. Analysis of experimental data has resulted in the conclusion that for a given set of conditions, the L values of the "tail end" of exiting photons increase in nearly exact proportionality to the increased optical density. It is observed that over 50% of the exiting photons from the human brain observe this law of proportionality. Thus, this law is directly applicable to living tissues, showing that a change of u is equal to the product of the change in extinction coefficient, E, exhibited at a particular wavelength and the change in the concentration, C, of a particular pigment. Thus, a change in concentration ΔC can be calculated from:

$$\Delta C = \frac{1}{\Delta EL} \Delta \left( \log \frac{I_o}{I} \right)$$

Therefore, the determination of the absolute concentration of absorptive pigments requires a knowledge of u at an isosbestic wavelength where no absorption change is observed, as in the wavelengths chosen for the dual wavelength system described above. If, for example, u is the same at a pair of closely spaced wavelengths at which the tissue pigment exhibits a detectable value of Δu, the concentration can be determined for a pigment such as deoxyhemoglobin, in which the spectrum has a number of isosbestic points. The value of u at an isosbestic point is taken as representative of a baseline value, while the value of u at an adjacent wavelength, where the change in absorption between oxy- and deoxy-hemoglobin is detectable, gives the concentration from the difference of the two u values:

$$u\ \text{lambda}_2 - u\ \text{lambda}_1 = (\Delta E(\text{lambda}_2 - \Delta E\ \text{lambda}_1) \times C$$

where $\text{lambda}_1$ and $\text{lambda}_2$ are two different wavelengths, and E is the extinction coefficient, from which C is determined on an absolute basis.

Many permutations, known to those of ordinary skill, of the derivation of the absolute concentration of an absorptive pigment set forth above are feasible. For example, multi-wavelength techniques in which the mixtures of absorptive pigments are deconvoluted appropriately may be employed.

Referring to FIG. 1, there is illustrated a block diagram showing the major components of a preferred embodiment of apparatus for carrying out the methods of the present invention. Initially, a 2 MHz signal is input to a mode-locking circuit to achieve short pulse widths. The signal from the mode locking circuit is in turn connected to a cavity dumped neodymium yttrium-aluminum-garnet (YAG) laser 10 to determine the pulse characteristics. The cavity dumped neodymium YAG laser 10 is used to excite a liquid dye laser 20 and generate short light pulses by cavity dumping. A 4 MHz signal is injected into the output pulse of the YAG laser 10 prior to its introduction into the liquid dye laser 20. Thus, in a preferred embodiment, the YAG laser 10 acts as a mode-locked exciter which is frequency doubled to 532 nm and excites a flowing stream of Syril dye (LDF 751, Exciton, Inc.) resulting in the activation of the liquid dye laser and producing a pulse having a wavelength of 760 nm with a repetition rate of 4 MHz. Depending upon the desired output frequency, the liquid dye laser also may preferably contain dyes ranging from styryl (760 nm) to Rhodamine 6G (630 nm). In a most preferred embodiment, a pulse train about 6 picoseconds ($6 \times 10^{-12}$ sec) in duration, and of an average intensity of about 30 milliwatts (mW) is generated.

The light pulses are coupled to the subject 30 via input light guide 22 and output light guide 24. In FIG. 1, the light guides 22,24 are shown affixed to the head of a subject 30 in order to determine the oxygenation state of the brain, however, the methods and apparatus of the present invention are also useful for determining the oxygenation state of other tissue regions and for determining the concentrations of other tissue pigments, such as myoglobin, which have known absorptive characteristics. In a preferred embodiment, the light guides 22,24 are flexible fiber optic guides, about 3 millimeters (mm) in diameter. It has been found through experimentation that exiting photons can be accumulated from points 2–10 centimeters (cm) apart on the circumference of the head, particularly the forehead. Therefore, when used on the forehead of a subject, as shown in FIG. 1, the distance between the input light guide 22 and the output light guide 24 should be between about 2 to 10 cm.

A detector 26 is connected to the output light guide 24. Preferably, the detector employed is a micro-channel plate detector. The detector 26 is in turn connected to a photomultiplier 40, for intensifying the signal. As will be understood by those of ordinary skill, the micro-channel plate detector 26 will have adequate gain, and preferably has time resolution on the order of about 50 picoseconds. Since the rise and fall times of the observed light pulse occur between 1.5 and 3.5 nanoseconds (ns) following the input pulse, in a preferred embodiment a 12 micro-channel plate, two-stage photomultiplier (e.g., Hamamatsu) provides an appropriate time resolution of approximately 100 picoseconds (0.1 ns), as required for these studies. A photomultiplier tube high voltage source 70 is also connected to the photomultiplier 40.

The output of the photomultiplier 40 is connected to a photon counting system in which roughly 100 "time bins" are employed, to accumulate the number of photons received over a period of between about 30 to 60 seconds. While in this mode of operation, only a single photon can be accepted per bin at any given time, thus total count rates of up to 40,000 per second are feasible without significant loss due to "pile up" or overburdening of the queue waiting to be received. The time course of the input/output pulse amplitude is thereby obtained. The output of the photomultiplier 40 is then fed to a photon counting system, preferably comprised of a constant fraction discriminator 50, which is a pulse amplitude discriminator in which the threshold for acceptance of a pulse is a constant fraction of the peak amplitude of the pulse. The signal is next input to a time to amplitude converter or scintillation counter 60, which produces an output pulse whose amplitude is proportional to the time difference between start and stop pulses. A multi-channel analyzer 70 and a personal computer 80 perform the final processing to convert the signal into a display format 90 or other data set.

The input pulse waveform is obtained by coupling the two fibers together through a simple optical attenuator. The output obtained by coupling the fibers to the forehead, for example, may be plotted graphically, the number of counts per channel preferably displayed on a time scale of about 1–5 nanoseconds ($1-5 \times 10^{-9}$ sec); the attenuation of the signal to $10^{-4}$ or $10^{-5}$ (40–50 dB) of initial intensity reached at about 5 nanoseconds following the input of the first pulse.

Thus, the pulsed light system of the present invention inputs a near-instantaneous light pulse into a tissue region and then detects the waveform of the "output" light intensity. This output rises to a maximum and then decays. In the presence of light absorptive materials, including tissue pigments such as hemoglobin and myoglobin, the decaying portion of the detected output is dominated at relatively long times by an exponential form:

$$I(t) = I_o \exp(-2.303\ kt) \qquad (1)$$

which is another expression of the generalized Beer-Lambert Law:

$$I(t) = I_o \exp(-2.303\ E[C]L) \qquad (2)$$

or more simply:

$$u = \frac{1}{L} \log \frac{I_o}{I} = EC \qquad (3)$$

where E is the extinction coefficient, C is the concentration of the absorber, u is the specific absorption per unit length and L is the path length. The path length is simply related to t, the time required for light to traverse a given length, i.e., the "time of flighty", by the equation:

$$L = ct/n \qquad (4)$$

where c is the velocity of light in the medium of interest and n is the medium's average refractive index. For example, for water these values are about n=1.33 and c=23 cm/ns.

In a semi-logarithmic plot of the detected light intensity, a approximately straight line with a negative slope is obtained. Since:

$$\log \frac{I_o}{I} = ECL = EC\frac{ct}{n}$$

This slope, u, is defined as:

$$u = \frac{1}{L} \log \frac{I_o}{I} = \frac{n}{ct} \log \frac{I_o}{I} = EC \quad (5)$$

In order to observe changes of absorption, for example, due to deoxygenation of oxyhemoglobin ($HbO_2$), then the concentration of the absorber may be calculated from the change in slope u:

$$\Delta C = \frac{\Delta u}{\Delta E} \quad (6)$$

From the Beer-lambert Law, an expression relating the optical density (OD) of the light to the concentration of the absorber may be derived:

$$OD = \log \frac{I_o}{I} = E[C]L \quad (7)$$

And accordingly, from equation (6), the concentration of an absorptive pigment, C, may be calculated:

$$\Delta C = \frac{\Delta u}{\Delta E}$$

Thus, it is now possible to determine the path length the photons travel by measuring changes in optical density and changes in concentration of an absorptive constituent in accordance with the methods and apparatus of the present invention. The following Examples illustrate both applications of the present invention and its use in conjunction with a CW system. See also, Chance, B. et al., "Comparison of time-resolved and -unresolved measurements of deoxyhemoglobin in brain", 88 Proc. Natl. Acad. Sci. USA (Biochemistry) 4971–75 (July 1988), which is incorporated by reference as if fully set forth herein.

EXAMPLE I

Figure 2:
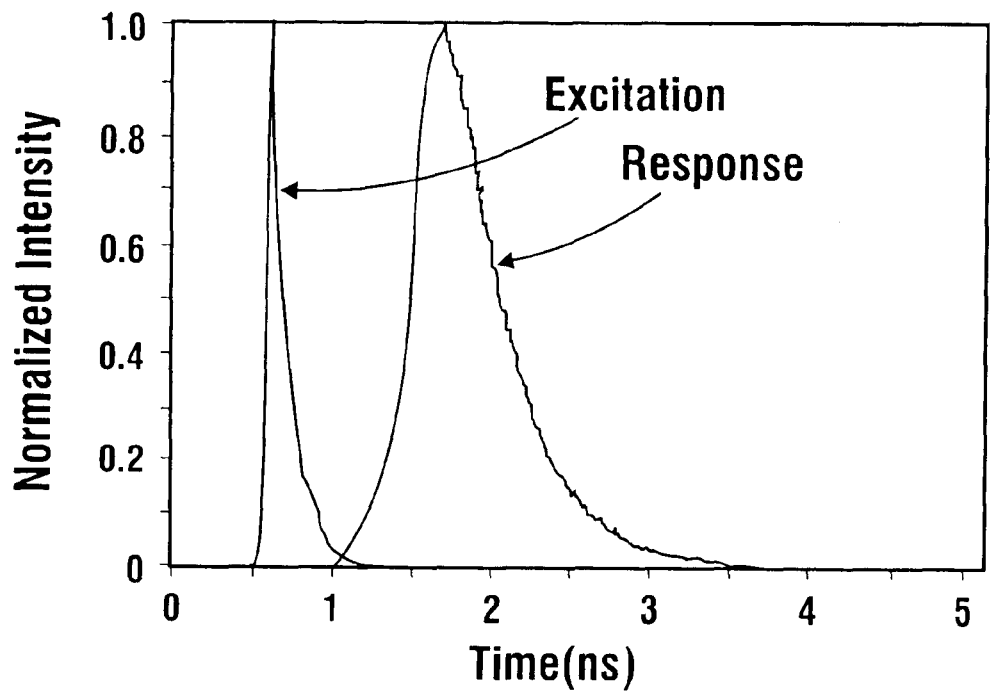
FIGS. 2 and 3 depict a plot of data describing intensity vs. time for light pulses collected from a human brain using the methods and apparatus of the present invention.
Figure 3:
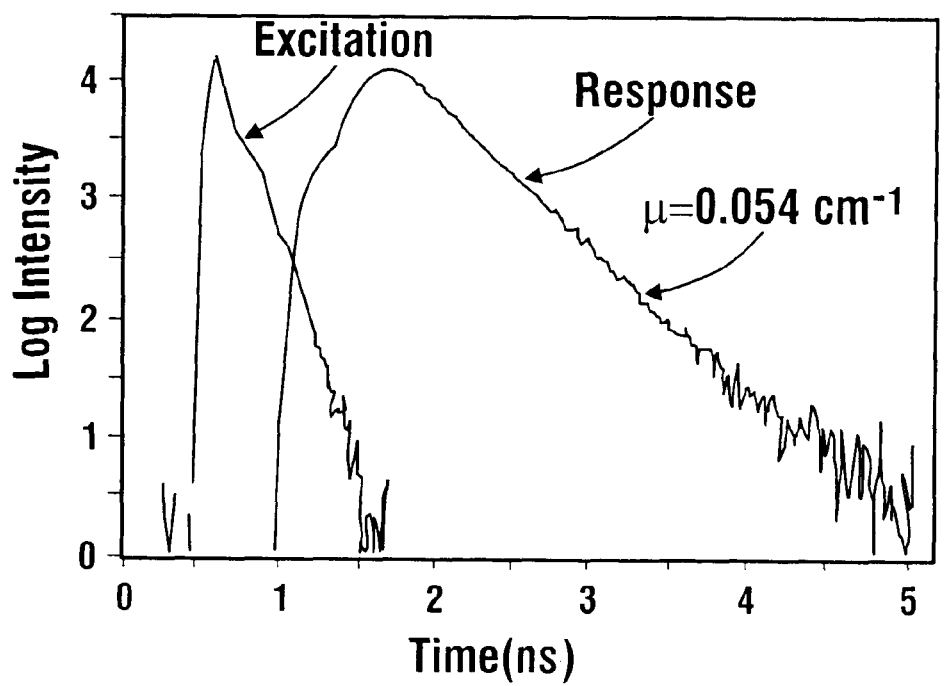

The performance of the apparatus described above is shown in FIGS. 2 and 3. These results are taken from a human brain. The display of the waveform of the initial pulse excitation, as shown in FIG. 2, is obtained by coupling the fibers together through a $10^{-4}$ (40 dB) attenuator: the waveform of the response is plotted on an amplitude vs. time on a linear scale. In FIG. 3, the same data are shown, however, the absorption data are now plotted on a logarithmic scale ($\log_{10}$). These results indicate that:

$u=1/L \log I_o/I$ is constant for the larger part of the decay intensity of the exiting photons, i.e., between about 2–5 ns.

EXAMPLE II

Figure 4:
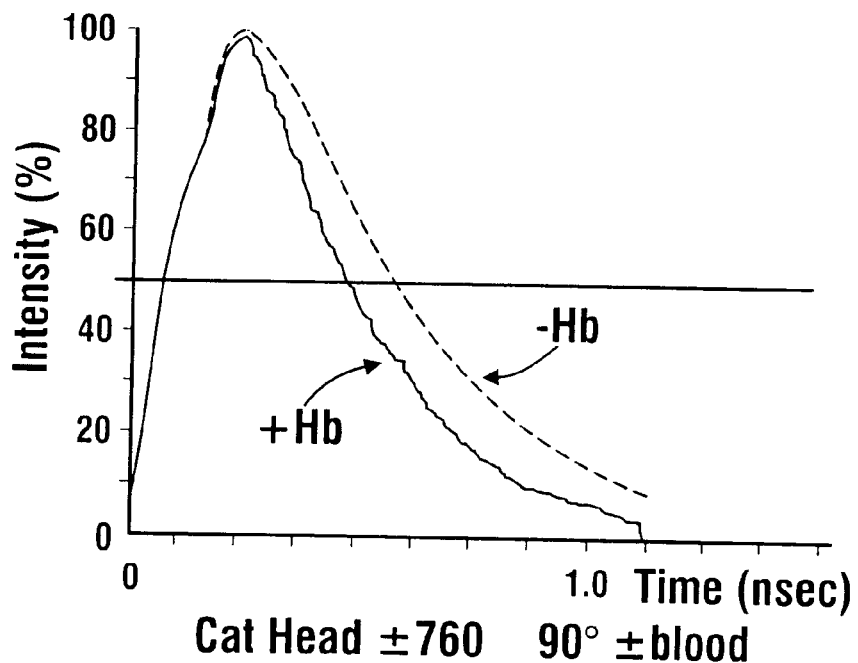
FIGS. 4 and 5 represent a plot of intensity vs. time of light pulses in a cat brain before and after an infusion of hemoglobin.
Figure 5:
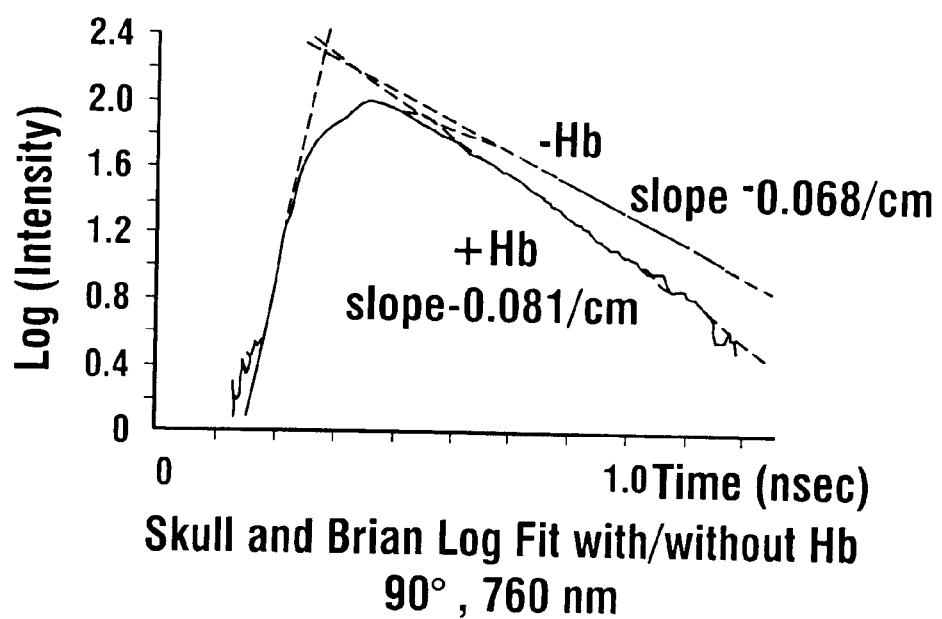
Figure 6:
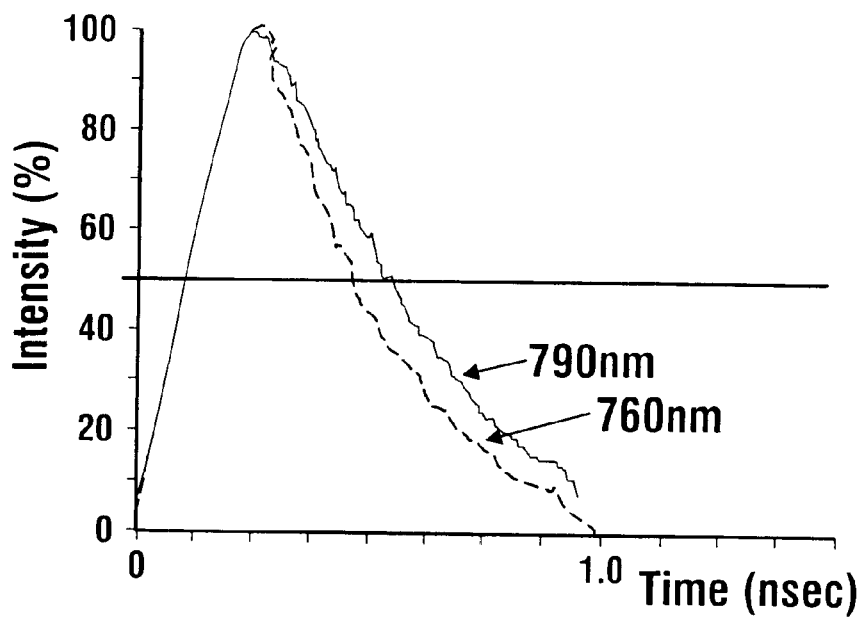
FIGS. 6 and 7 represent a plot of intensity vs. time for a cat brain illustrating the effect of wavelength on decay kinetics.
Figure 7:
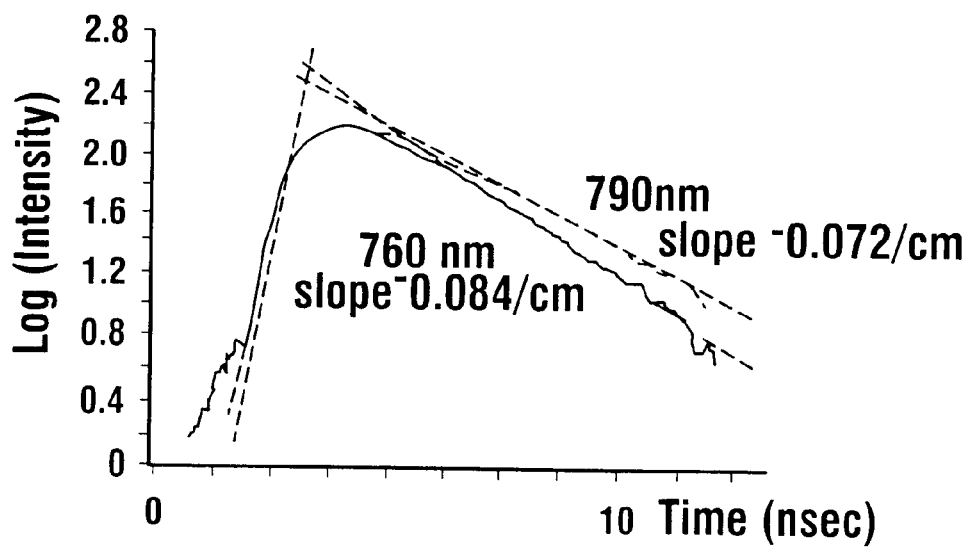

FIGS. 4–7 depict the results of data taken from a preserved cat brain which has had hemoglobin injected into the contralateral hemisphere. FIG. 4 and FIG. 5 show that the value of u is increased by the injection of hemoglobin into the contralateral hemisphere. FIG. 6 and FIG. 7 illustrate that an increment of absorption is much greater in the injected cat head when a wavelength of about 760 nm is used instead of about 790 nm, the absorption being much greater at the former wavelength.

To measure penetration depths in the brain, the time resolution of the photon migration within various tissues and the models was evaluated. The absorption of visible and NIR light in highly scattering material has been described in the literature. See Duysens, L. *Prog. Biophys. Mol. Biol.* 14, 1–104) (1964); Chance, B., et al., *Nature* (London) 195, 1073–1075 (1962); Chance B. *Nature* (London) 169, 215–230 (1952); Blumberg, W. E. *Biophys. J.* 51, 288 (1987) (abstr.); vanderZee, P. & Delpy, D. T. *Oxygen Transport to Tissue X*, eds. Mochizuki, (Plenum, New York), pp. 191–197 (1988) and Bonner, R. F., et al. *J. Opt. Soc. Am.* Sec. A 4, 423–432) (1987). Light is multiply scattered so that directionality is lost after a few scattering lengths. See Blumberg, W. E. *Biophys. J.* 51, 288 (1987) (abstract). Thus, the duration of a short pulse of radiation introduced into a highly scattering object, such as the brain, is observed to be greatly prolonged because of the long path of photon migration to the receiver site. When there is a specific absorber such as Hb (measured at 760 nm), the number of photons detected will be appropriately diminished.

In this Example, two synchronously pumped, tunable dye lasers (Coherent Laser Products Division), operating at 760 and 790 nm and pumped by the second harmonic of a CW NdYAG (neodymium/yttrium/aluminum-garnet) mode-locked laser, were used as the light source. The pulse length was about six picoseconds (6.0 ps), the pulse energy was 1.3 nJ per pulse, and the average power was 100 mW at 77 MHz. The decay of the radiation was recorded with a 0.2-cm fiber-optic probe coupled to a streak camera (Hamamatsu). The fibers were placed at various positions with respect to the input light to record the migration of light to the exit fiber. The velocity of light, c/n, in the brain tissue is taken to be 0.023 cm/ps for a refractive index of 1.3. The signal-to-noise ratio was adequate for 3 decades of logarithmic plot. The time-difference determinations are accurate to 10 ps.

Figure 8:
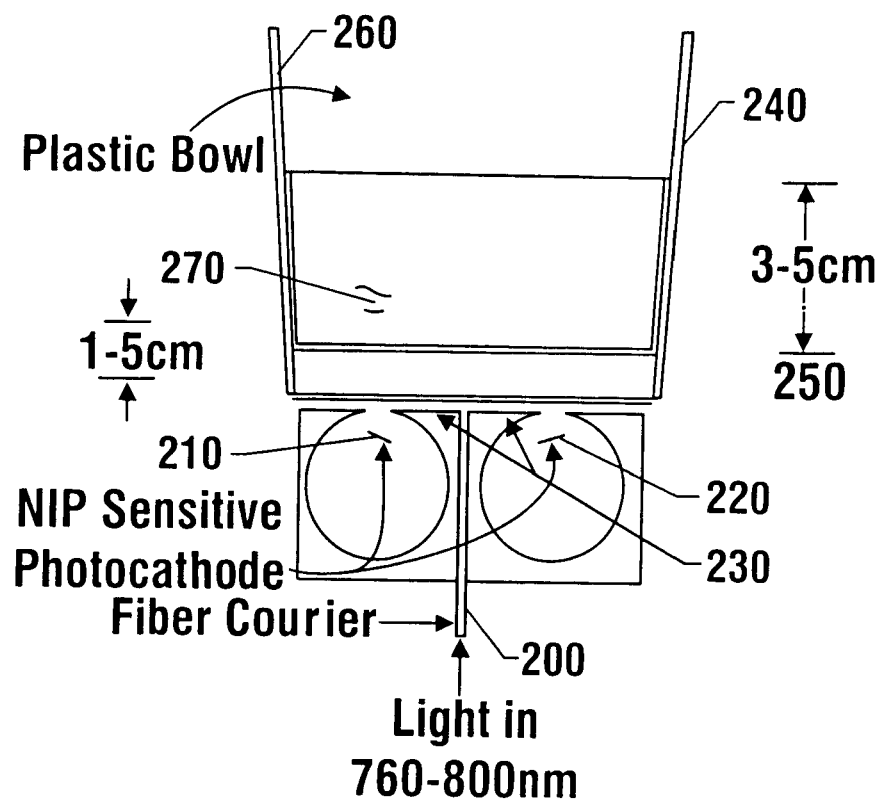
FIG. 8 is a partially schematic depiction of a continuous light spectrophotometer.
Figure 9:
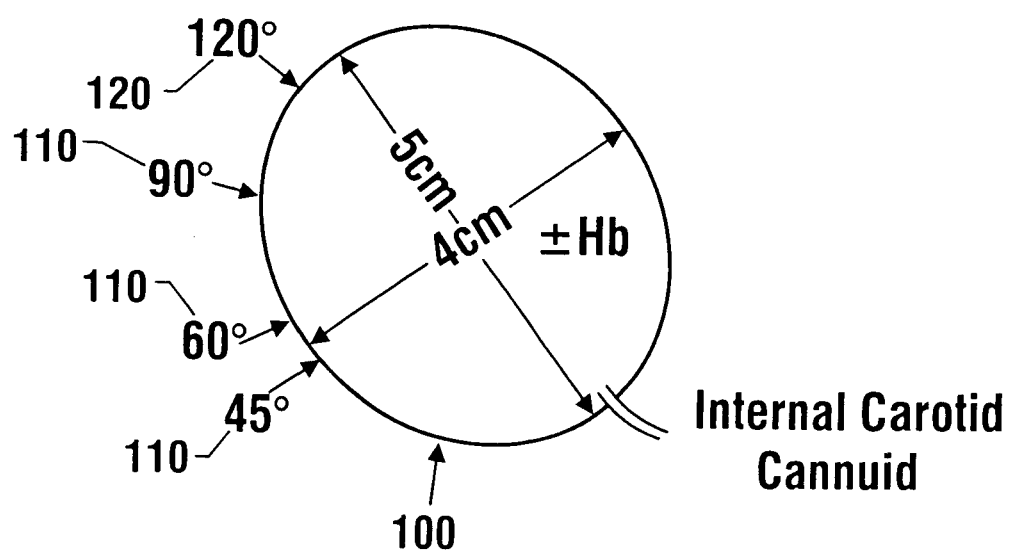
FIG. 9 is a schematic of a cat's head, showing the relative angles at which excitation and detection ports are located.

The geometry of the cat-head model used in this Example is illustrated in FIG. 9, which indicates the point of input 100 of the laser light and the points 110,120, at which a 0.2 cm diameter fiber probe was attached to obtain output signals. The points 110,120 were chosen to correspond to the 2.0 cm separation of the milk model illustrated in FIG. 8 and three additional 3.0, 5.0, and 6.5 cm points at angles of 45 degrees, 60 degrees, and 90 degrees and 110 degrees, respectively.

To evaluate the changes of photon migration that occur when a known concentration (0.15 mM) of Hb is added to a localized region of a brain, the model used met the following requirements: (i) the brain was initially hemoglobin free,(ii) there was a portion of brain into which Hb could be injected and in which Hb would be stable, (iii) the brain could be observed without or with the skull, and (iv) it could be transported readily. This model involves redistribution of $K^+$, $Na^+$, and $H_2O$ that occur on death. However, the values of the logarithmic slope do not differ greatly from the in vivo condition; 0.08 as compared to 0.07 $cm^{-1}$.

The animal was anesthetized with ketamine and heparinized (400 units/kg of body weight). The head was cleared of blood by exchange transfusion with Ringer's solution, which was followed by 10% (vol/vol) glycerol. Experimental observations were made before and after perfusion of one hemisphere (via the cannulated carotid artery) with Hb in blood cells at a normal hematocrit (40%). Subsequent analysis of the distribution of the hemoglobin showed 0.035 mM and 0.063 mM in the two hemispheres after reperfusion with blood.

FIGS. 4 and 5 show data obtained from a cat head before and after Hb injection at an angle of 90 degrees, which corresponds to a 4.2-cm distance between light input and output. In the absence of Hb, the half-width or scattering-time constant was 450 ps. When Hb was added to the contralateral hemisphere, a value of 360 ps was obtained. Referring to FIG. 5, the values of the logarithmic slope are 0.068 cm$^{-1}$ and 0.081 cm$^{-1}$, and $L_{1/2}$ values were 6.7 and 4.8 cm, respectively.

FIGS. 6 and 7, the effect of wavelength upon the decay kinetics was measured at 760 and 790 nm. The angle between incidence and recording was 90 degrees. The specificity of wavelength dependence is shown; it is observed that the waveform decays more rapidly with 760-nm light than with 790-nm light. The scattering time constant at 790 nm is 430 ps, which decreases to 350 ps at 760 nm. Referring to FIG. 7, the logarithmic slope values are 0.072 and 0.084 cm$^{-1}$, and the $L_{1/2}$ values are 5.8 and 4.2 cm, respectively.

EXAMPLE III

In order to compare the results achieved by the present invention with other systems, a continuous wave system, as illustrated in FIG. 8 was used. In this system, continuous wave excitation at 760 and 800 nm was time-shared through a single fiber-optic light guide 200. The detectors 210,220 (Hamamatsu R928) have a high signal-to-noise ratio because of their measurement of light emitted from a large area (2 cm$^2$ per detector). Light input and output were separated by 2 cm. A barrier 230 was used to minimize specular and short path reflections. See, U.S. patent application Ser. No. 266,166, filed Nov. 2, 1988, entitled, "Optical Coupling System For Use In Monitoring Oxygenation State Within Living Tissue", which is incorporated herein by reference as if fully reproduced herein.

The important spectral parameters of HbO$_2$ and Hb required are the differences between their extinction coefficients at 760, 790, and 800 nm. These are 0.25, 0.086, and greater than 0.01 cm$^{-1}$ mM$^{-1}$, respectively. At a typical brain Hb value of 0.15 mM, a logarithmic slope of 0.038 cm$^{-1}$ at 760 nm would be expected in a cat brain on deoxygenation with normal hematocrit and no light scattering. Therefore, $u=0.25\times 0.15=0.038$ cm$^{-1}$.

To simulate the presence of the skull and to quantify the detection of HbO$_2$ deoxygenation within a light-scattering volume, a model as shown in FIG. 8 was used. The use and verification of this type of model for these studies can be found in the literature, See vanderZee, P. & Delpy, D. T., *Oxygen Transport to Tissue X*, eds. Mochizuki, M., et al. (Plenum, New York), pp. 191–197 (1988) and Tamura, M. H., et al., *Chemoreceptors and Reflexes in Breathing*, ed. Lahiri, S. (Oxford, New York),(1987), in press. The larger vessel 240 (5.5-cm diameter) is filled with a tissue substitute 250 (artificial milk derivative) adjusted to mimic the NIR light-scattering property of the skull. Inside this container is a second vessel 260 containing 0.10–0.20 mM Hb and bakers' yeast 270 with an equivalent scattering power to simulate the blood-perfused brain tissue, 5–10% by weight. The yeast respiration causes a continuous deoxygenation of HbO$_2$ so that determination of its absorption changes simulates anoxia in the brain. The internal vessel 260 is moveable with respect to the external one 240 so that a scattering volume of variable depth is interposed between the two.

Figure 10:
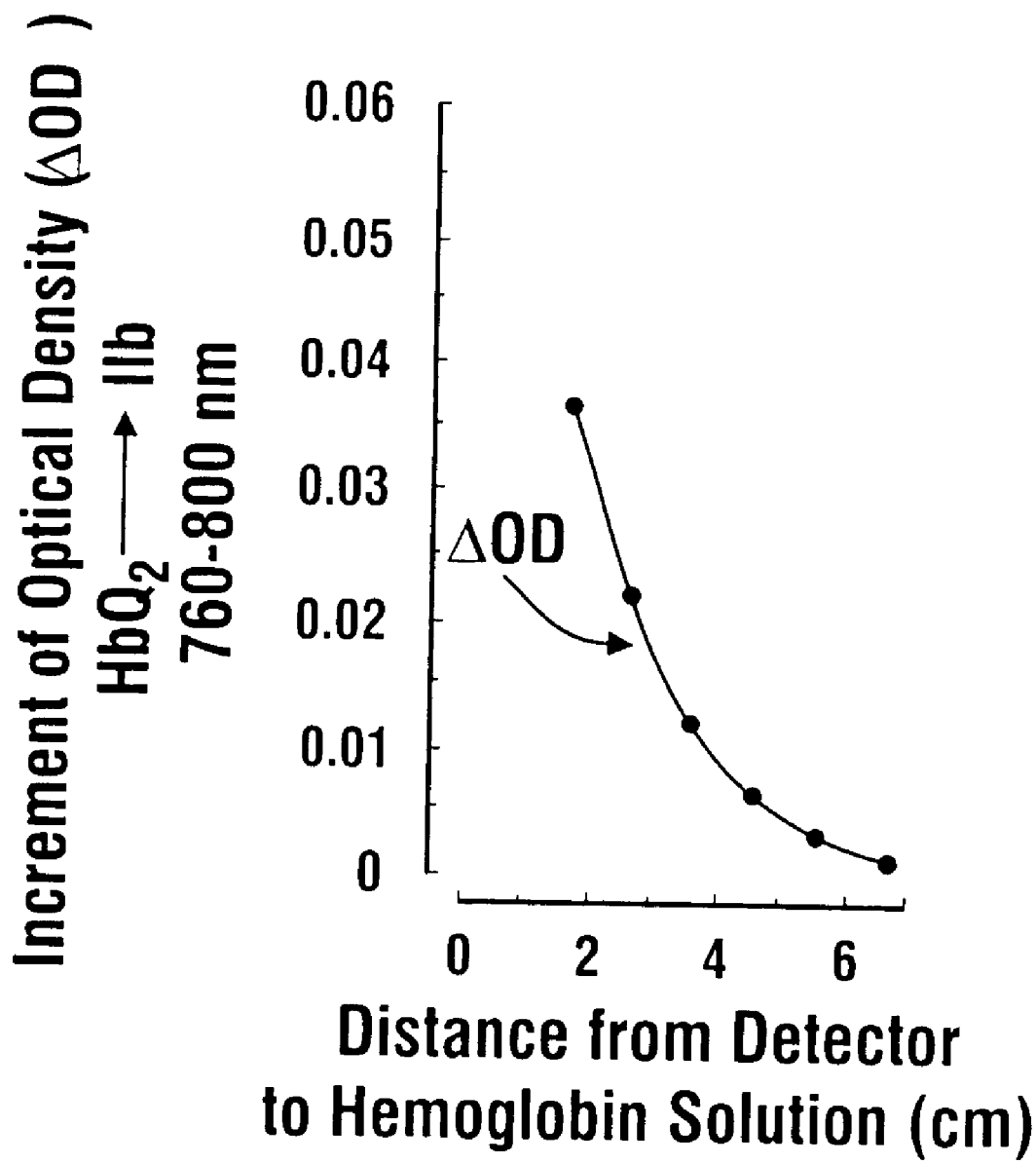
FIG. 10 depicts the effect of distance between the light input and the hemoglobin containing compartment, derived using the apparatus illustrated in FIG. 8.

Since the effect of distance between the light input 100 and the hemoglobin-containing compartment can be varied in the model system shown in FIG. 8, a plot of tire signal caused by deoxygenation of 0.20 mM HbO$_2$ can be displayed as a function of optical path through the milk substitute. The Hb/HbO$_2$ signal decreases logarithmically as the length of the optical path through the milk substitute-containing vessel 240 was increased from 2 to 7 cm. This result can be observed by referring to FIG. 10. The slope is 0.014 cm$^{-1}$, and the change in optical density extrapolated to zero thickness of the milk layer was 0.06. This may be compared with a logarithmic slope value of 0.050 cm$^{-1}$ as calculated from the increment of the extinction coefficient (0.25 cm$^{-1}$, mM$^{-1}$) with 760 nm as a measuring wavelength and 800 nm as a reference wavelength. (see Table 1, discussed below)

EXAMPLE IV

Further results were derived using a system constructed in accordance with the present invention applied to the temporal region of the head of a volunteer human subject. Breathing graded decreases of oxygen caused the subject's HbO$_2$ to become partially deoxygenated, as shown in FIG. 11A. The subject's electroencephalogram (EEG) was also monitored and showed corresponding changes as oxygen delivery decreased, as seen in FIG. 11D. The EEG began to show altered activity as the inspired oxygen (FiO$_2$) decreased to 0.10. The changes became marked at an FiO$_2$ of 0.065, and this corresponds to the lowest degree of hemoglobin saturation. Immediately upon the subject's breathing room air, all parameters returned rapidly to normal. The total change in optical density at 760 nm with respect to that at 800 nm, was 0.18. The concentration change cannot be calculated without an estimate of L, the effective path length. For the expected value for 0.15 mM Hb, the apparent optical path as measured by the time-resolved spectroscopy methods of the present invention is about 9.6 cm, corresponding to a concentration change of $0.18/(0.25\times 9.6)=0.076$ mM.

Figure 11:
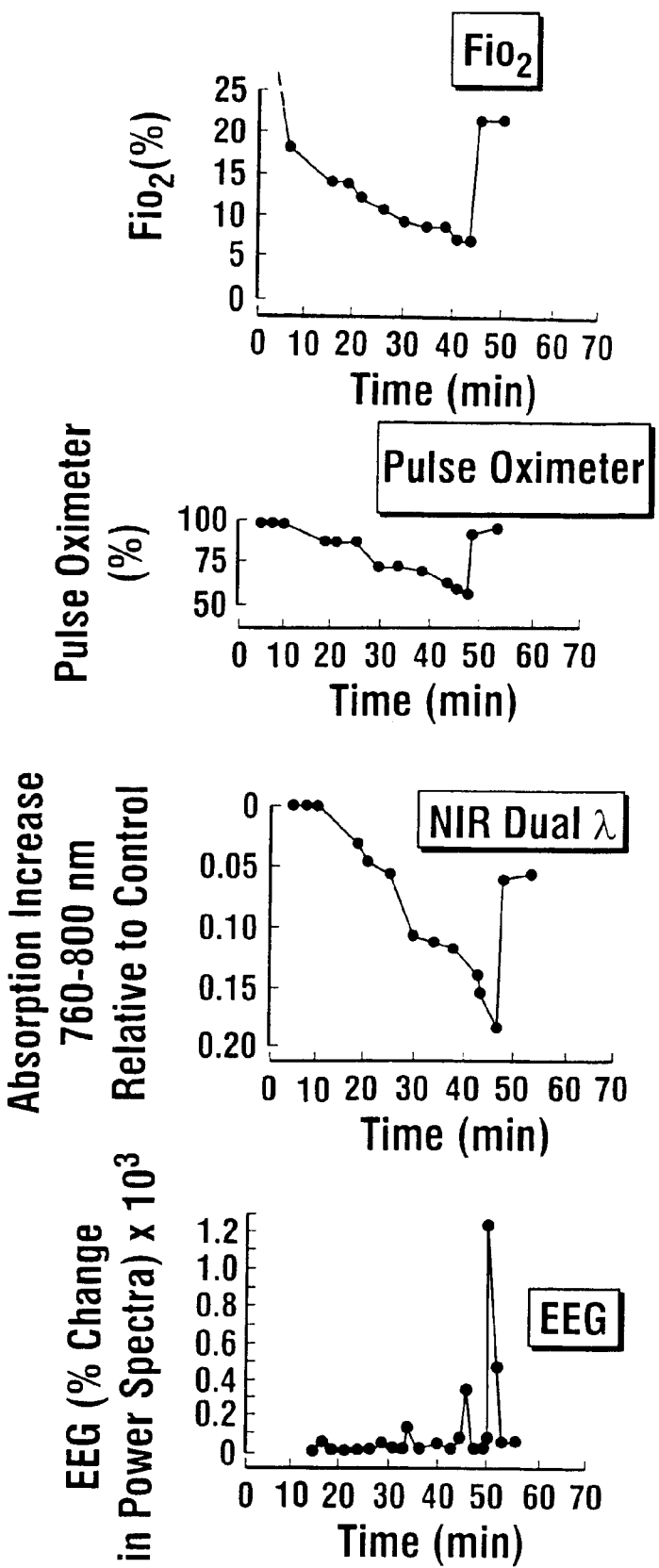
FIG. 11 compares inspired oxygenation and EEG data from a human brain, as measured by different systems.
Figure 12:
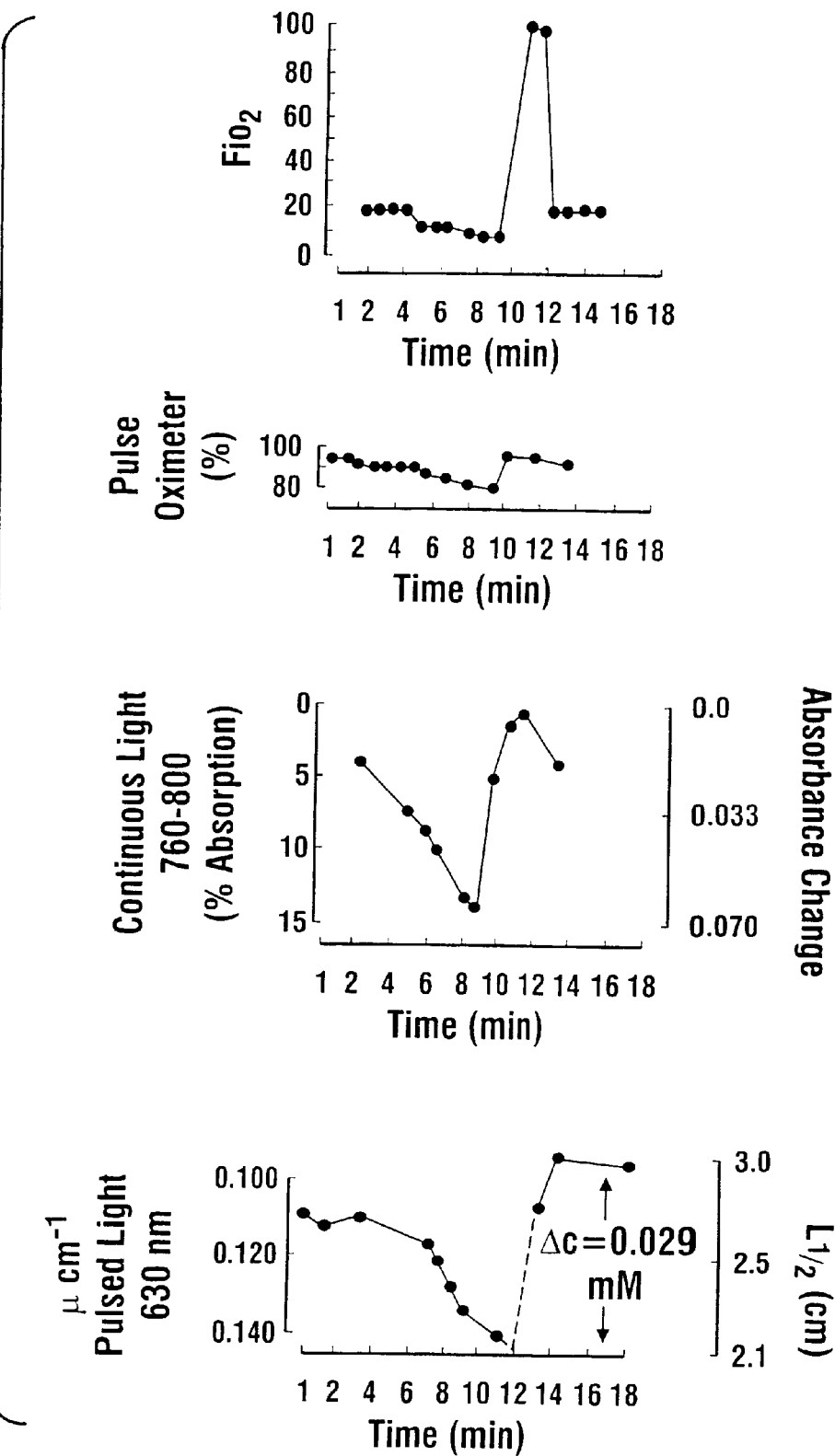
FIG. 12 compares inspired oxygenation and pulse oximeter data with results obtained from both continuous and time resolved systems.
Figure 13:
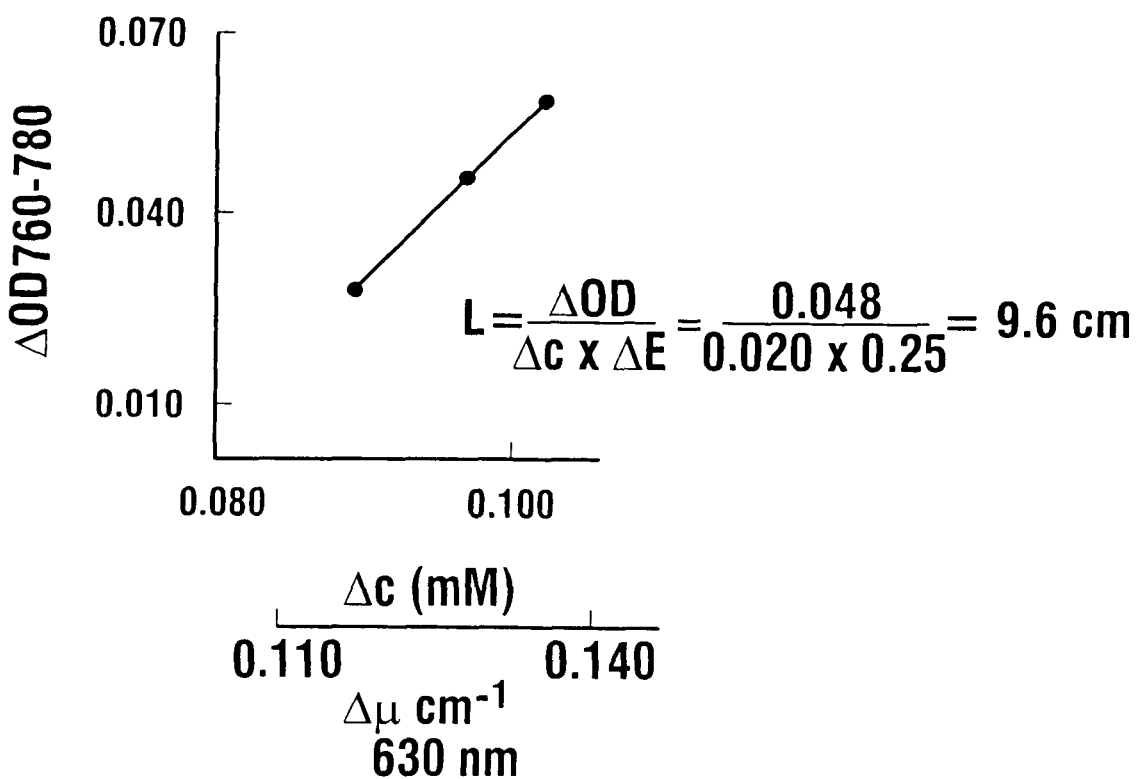
FIG. 13 illustrates an example of the derivation of the path length from time-resolved data.

FIG. 11 shows that the results derived from data collected using continuous light spectrophotometry systems correlate well with physiological and biochemical parameters. As illustrated by FIGS. 12 and 13, the time-resolved spectroscopy methods of the present invention have the capability to determine the optical path length for a given application of a continuous light spectrophotometry system. The data shown in FIGS. 12 and 13 were collected from a patient undergoing hypoxia by breathing nitrogen, as indicated by the mass spectrographic recording of the fraction of inspired oxygen (FiO$_2$). The breathing of nitrogen impacts upon the pulse arterial saturation only mildly, as illustrated by FIG. 12B. Thus, merely viewing the pulse oximeter data by itself, the brain would be expected to be normally oxygenated. However, the direct measurements which are indicated in FIGS. 12C and 12D reveal that, in fact, an entirely different situation exists. FIG. 12C depicts the results obtained from the application of a continuous light system to the left forehead. These data show a continuous deoxygenation of the brain as the hypoxia becomes more severe. Continuous light spectrophotometry, see FIG. 12C, shows a change of absorption of 0.04 OD units as compared with FIG. 11C, a less severe, but significant hypoxia. FIG. 12D illustrates results obtained on the right hemisphere by the time-resolved spectroscopy system of the present invention. The values of u, in this case measured at 630 nm, are exemplary of the ability of the present invention to operate effectively in a wide range of wavelengths. In addition, FIG. 12D shows decreases which become more abrupt as the hypoxia increases. $\Delta u$ is 0.03 cm$^{-1}$.

One of ordinary skill will note the general parallelism between the two spectrophotometry methods, although the initial phase is less impacted upon, as measured by the longer migration distances of the pulsed light system. Knowing the extinction coefficient of hemoglobin at 630 nm, a total concentration change of 0.029 mM may be calculated. It is noteworthy that a greater degree of hyperemia is detected by continuous light than pulsed light; it is suspected that this is because the hypermia may be more prominent in the superficial layers to which the continuous method responds, while the pulses of light used in the time-resolved system probe the brain to greater depths.

Referring now to FIG. 13, there is illustrated a plot having the absorptive changes (changes in OD) measured by the continuous light system as the ordinate, and the concentration changes measured using the pulsed light system of the present invention also placed along the ordinate. These correlate well in the region of rapid change, and the slope of the line is calculated to be about 9.6 cm. Thus, the mean path length of the continuous light system may also be calculated to be about 9.6 cm and the concentration change, $\Delta c$, measured over this region is 0.020 mM.

Summary of Model Systems

The results obtained from the models and systems discussed above are collected in Table 1. Table 1 provides a number of properties of the light-pulse output of several models to a picosecond-light-pulse input. The outputs are evaluated by several criteria: the pulse width; the angle between light input and output (Table 1, column 3; and FIG. 9); the logarithmic slope, and $L_{1/2}$. The short pulse observed in reflection from a surface in water (40 ps) was broadened to 110 ps in the milk model, to nearly 500 ps in the preserved cat brain and in the adult human brain. The criterion of interest here is the slope of the experimental decay (Table 1, column 6).

In Table 1, values of logarithmic slope for a variety of angular positions and distances on the circumference on the brain, all measured with respect to the input pulse are summarized. In the cat brain of Example II, 45 degrees and 60 degrees gave the same result, and 90 degrees gave a 20% increase of lifetime (a 20% decrease of slope). The corresponding separations are 2.0, 3.0, and 5.0 cm. Thus, the decay rate of light observed does not depend critically upon the location of the fibers. This validates that the 2.0-cm separation of input and output used with the continuous illumination of the human brain, gives a penetration of 50% of the emitted light to several centimeters.

The studies with pulse-light illumination establish the potential of the two wavelength approach to in vivo NIR reflectance spectroscopy. FIG. 11 demonstrates that the CW measurements correlate with changes in the EEG, which also a measure of brain oxygen availability during hypoxia. The difference between NIR spectroscopy of the human head and visible spectroscopy of the finger (pulse oximeter) is consistent with the above suggestion that the NIR data represent brain arteriole-venule capillary hemoglobin, while the pulse oximeter measures peripheral arterial saturation. Deoxygenation in the adult gives a change in optical density of at least 0.18. The high rate of oxygen utilization of the brain affords a high sensitivity of brain capillary oxygen content for the detection of early ischemia.

The NIR CW signals (2.0 cm$^2$ area for each detector in the milk model) give an apparent logarithmic slope of 0.06 cm$^{-1}$ for the detection of hemoglobin signals in the model of FIG. 8. However, the hemoglobin concentration is underestimated by interposing the non-hemoglobin containing barrier—a loss of about 25% per cm. The pulsed-light data for the milk model give a logarithmic slope of 0.083 cm$^{-1}$. The cat brain gives a logarithmic slope equal to 0.081 cm$^{-1}$ a value similar to that of the milk model. The latter values change only 20% when the spacing of the light input and output is increased from 2.0 to 5.0 cm. The human head gives a logarithmic slope of 0.07 cm$^{-1}$ and $L_{1/2}$ equal to 4.0 cm. These values suggest the applicability of the milk model and the cat brain model to the CW data of FIGS. 10 and 11. Thus, it appears that a simple dual-wavelength CW spectrometer, as shown in FIG. 8, can measure the state of hemoglobin oxygenation within the brain, once the path length has been calibrated.

It ha been found that boundary conditions have a large effect upon the apparent length of photon diffusion. Surprisingly, the effect of reflections from the skull is large and prolongs the half-time from 290 to 470 ps at 90 degrees, producing an increase in the $L_{1/2}$ values from 3.3 to 5.6 cm. Artifactual reflections, due to the frontal sinuses are readily observed, and fast passage through the subarachnoid space, is observable. In fact, when the spacing of input and output exceeds 10 cm, the $L_{1/2}$ appears to decrease, suggesting that "transcranial" geometries may be suboptimal and artifactual. See Jobsis, et al. *J. Appl. Physiol.* and Jobsis, et al. *Adv. Exp. Med. Biol.*, supra.

The present invention allows quantitative results to be obtained in scattering tissues. Table 1 shows two types of perturbations of the logarithmic slope, by the presence or absence of concentration of hemoglobin (Hb and $HbO_2$), and, by a change of wavelength. In the center portion of the milk model shown in FIG. 8, the $Hb/HBO_2$ (0.15 mM Fe) change at 760 nm gives a change in logarithmic slope of 0.022 cm$^{-1}$. In the contralateral portion of the brain shown in FIG. 9, the injection of 0.15 mM Hb gave a logarithmic slope of 0.023 cm$^{-1}$. That these are specific absorption effects is supported by the change of wavelength from 760 to 790 nm; the change in the logarithmic slope is 0.017 and 0.002 cm$^{-1}$ mM Hb and $HbO_2$, respectively. In the cat brain, the change in the logarithmic slope is 0.011 cm$^{-1}$ corresponding to a concentration of 0.44 mM as compared with 0.35 and 0.65 mM in the two hemispheres, or 0.50 mM. Since the goal of these experiments is to ensure the diffusion of light into the center of the milk model and into the contralateral hemisphere of the cat-brain model, it would be expected that only a fraction of the Hb added would be found. In the milk model, 0.09 mM is found (the change in extinction coefficient is equal to 0.25 cm$^{-1}$, mM$^{-1}$), and in the cat brain, 0.050 mM is found.

Thus, one would expect at least 0.15 mM hemoglobin would be found in FIG. 11 and that the path-length estimate of 5.0 cm is a good approximation for the 4.0 cm$^2$ aperture hemoglobinometer. The wavelength dependence of the scattering is too small to be detected when the wavelength is changed from 790 to 760 in the cat brain. Thus, the dual-wavelength determination of hemoglobin seems unaffected. It appears that the time-resolved method greatly increases the usefulness of optical spectroscopy in tissue.

The pulse-light study affords key information on the penetration obtained with the simpler CW method and validates input/output spacings of 2.0 cm and upwards for the simpler system. The detection of tissue volumes containing Hb is demonstrated by using time-resolved spectroscopy. In large objects, the requirements of a system may be relaxed to permit 20- to 50-ps input light pulses (available from NIR laser iodes in the IR region) to obtain the scattered light decay over 3 decades of intensity. Highly significant information appears to be available in the Beer-Lambert law dependence of the relaxation times, particularly for the detection of the concentration of the absorber and the value of the extinction coefficient. It appears that a deconvolution theorem based upon multiple wavelengths and multiple input/output sites may also shed light on the imaging problem.

What is claimed is:

1. A apparatus for spectroscopic examination of biological tissue, comprising:

a source of electromagnetic radiation pulses having a visible or near infrared wavelength, each pulse of said radiation having an input pulse waveform of duration of a nanosecond or less;

an input port constructed for introduction, into biological tissue having scattering and absorptive properties, pulses of said electromagnetic radiation;

a detection port constructed to receive radiation that has migrated over scatter paths in the scattering and absorptive tissue from the input port located several centimeters from the detection port;

a streak camera constructed and arranged to record at said wavelength said received radiation to obtain a detected pulse waveform formed by photons that have migrated over scatter paths in the tissue; and a processor arranged to determine a selected tissue property based on said detected pulse waveform at said wavelength and said introduced pulse waveform at said wavelength.

2. The apparatus of claim 1 wherein said processor is programmed to determine said selected tissue property based on a rate of decay of said detected waveform.

3. The apparatus of claim 1 wherein said processor programmed to determine a rate of decay of said detected waveform to calculate an absorptive property of a tissue constituent of interest.

4. The apparatus of claim 1 wherein said processor programmed to determine a time delay of said detected waveform.

5. The apparatus of claim 1 wherein said source emits said wavelength of 760 nm.

6. The apparatus of claim 1 wherein said source emits said wavelength of 790 nm.

7. The apparatus of claim 1 wherein said input port is positionable in contact with the tissue and said detection port is positionable in contact with the tissue.

8. The apparatus of claim 7 wherein said input and detection ports are arranged to have a relative orientation of about 60 degrees.

9. The apparatus of claim 7 wherein said input and detection ports are arranged to have a relative orientation of about 90 degrees.

10. A method for spectroscopic examination of biological tissue, comprising the act of:

introducing at an input port, into biological tissue having scattering and absorptive properties, pulses of electromagnetic radiation having a visible or near infrared wavelength, each pulse of said radiation having an input pulse waveform of duration of a nanosecond or less;

detecting, at a detection port, radiation of said wavelength that has migrated over scatter paths in the scattering and absorptive tissue from the input port located several centimeters from the detection port;

recording by a streak camera said detected radiation to obtain a detected pulse waveform formed by photons that have migrated over scatter paths in the tissue; and determining a selected tissue property based on said detected pulse waveform at said wavelength and said introduced pulse waveform at said wavelength.

11. The method of claim 10 wherein said selected tissue property depends on a time delay of said detected waveform.

12. The method of claim 10 wherein said wavelength is 760 nm.

13. The method of claim 10 wherein said wavelength is 790 nm.

14. The method of claim 10 wherein relative orientation of said input and detection ports is about 60 degrees.

15. The method of claim 10 wherein relative orientation of said input and detection ports is about 90 degrees.

16. The method of claim 10 wherein said selected tissue property depends on an optical pathlength of photons migrating between said input port located in contact with the tissue and said detection port located in contact with the tissue.

17. The method of claim 16 wherein said selecting different distances between said input port and said detection port to change the paths through which photons of said radiation migrate comprises using at least one said optical input port and at least one said optical detection port.

18. The method of claim 10 further comprising selecting different distances between said input port and said detection port to change paths over which photons of said radiation migrate.

19. The method of claim 18 wherein said using at least one said optical input port and at least one said optical detection port includes applying said ports at varying locations of the examined biological tissue.

20. The method of claim 10 wherein said selected tissue property depends on a rate of decay of said detected waveform.

21. The method of claim 20 wherein said rate of decay of said detected waveform is used to determine an absorptive property of a tissue constituent of interest.

22. The method of claim 21 wherein the tissue constituent is hemoglobin.

* * * * *